United States Patent [19]

Lange

[11] 4,379,065
[45] Apr. 5, 1983

[54] AMINO PHENOLS IN COMBINATION WITH ASHLESS ESTER DISPERSANTS AS USEFUL ADDITIVES FOR FUELS AND LUBRICANTS

[75] Inventor: Richard M. Lange, Euclid, Ohio

[73] Assignee: The Lubrizol Corporation, Wickliffe, Ohio

[21] Appl. No.: 358,510

[22] Filed: Mar. 15, 1082

Related U.S. Application Data

[63] Continuation of Ser. No. 253,830, Apr. 13, 1981, Pat. No. 4,320,021, which is a continuation of Ser. No. 914,710, Jun. 12, 1978, abandoned, which is a continuation-in-part of Ser. No. 892,529, Apr. 3, 1978, abandoned, which is a continuation-in-part of Ser. No. 676,172, Apr. 12, 1976, abandoned, which is a continuation-in-part of Ser. No. 622,358, Apr. 14, 1975, abandoned.

[51] Int. Cl.$^3$ .............................................. C10M 1/32
[52] U.S. Cl. ................................. 252/51.5 A; 44/58; 44/63; 44/71; 44/75
[58] Field of Search ...................... 44/58, 75, 63, 71; 252/51.5 R, 51.5 A; 564/418, 419, 422, 423, 428, 439

[56] References Cited

U.S. PATENT DOCUMENTS

| | | | |
|---|---|---|---|
| 4,100,082 | 7/1978 | Clason et al. | 252/51.5 A X |
| 4,200,545 | 4/1980 | Clason et al. | 252/51.5 A X |
| 4,320,020 | 3/1982 | Lange | 252/51.5 R |
| 4,320,021 | 3/1982 | Lange | 252/51.5 R |

*Primary Examiner*—Andrew Metz
*Attorney, Agent, or Firm*—Ronald L. Lyons; Raymond F. Keller; John P. Ward

[57] ABSTRACT

Amino phenols of the general formula

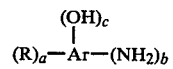

wherein R is a substantially saturated, hydrocarbon-based group of at least about 30 aliphatic carbon atoms, a, b and c are, for example, each 1, 2 or 3, and Ar is an aromatic moiety such as a benzene nucleus, naphthalene nucleus or linked benzene nuclei, are useful additives for fuels and lubricants. These amino phenols can be conveniently prepared by nitrating an appropriate hydroxy aromatic compound and reducing the nitro groups to amino groups. Typically such amino phenols are formed by nitration and reduction of alkyl phenols having an alkyl or alkenyl group of at least about 50 carbon atoms.

21 Claims, No Drawings

AMINO PHENOLS IN COMBINATION WITH ASHLESS ESTER DISPERSANTS AS USEFUL ADDITIVES FOR FUELS AND LUBRICANTS

REFERENCE TO RELATED APPLICATIONS

This application is a continuation of U.S. Ser. No. 253,830, filed Apr. 13, 1981, now U.S. Pat. No. 4,320,021, which is a continuation of U.S. Ser. No. 914,710, filed June 12, 1978, and now abandoned, which is a continuation-in-part of U.S. Ser. No. 892,529, filed Apr. 3, 1978, and now abandoned, which is a continuation-in-part of U.S. Ser. No. 676,172, filed Apr. 12, 1976, and now abandoned, which is a continuation-in-part of U.S. Ser. No. 622,358, filed Apr. 14, 1975, and now abandoned. The disclosures of these prior applications are hereby incorporated by reference into this application in their entirety.

BACKGROUND OF THE INVENTION

1. Field of the Invention

This invention relates to additive compositions for use in lubricants based on oils of lubricating viscosity and normally liquid fuels. More particularly, it relates to amino phenols having at least one hydrocarbon-based group of at least about 30 aliphatic carbon atoms.

2. Prior Art

U.S. Pat. No. 2,197,835 describes the formation of metal salts of aromatic amines, said amines being formed by nitration followed by reduction of wax-substituted, hydroxy-aromatic hydrocarbons. These metal salts can be incorporated in mineral oils to depress their pour points and increase their viscosity indices.

U.S. Pat. Nos. 2,502,708 and 2,571,092 both disclose the nitration and subsequent hydrogenation to an amine of cardanol. This amino cardanol is said to be useful as an anti-oxidant for mineral oils, fats and petroleum oils. Cardanol, also known as anacardol, is also said to be a mixture of 3-pentadecylphenol, 3-(8'-pentadecenyl)-phenol, 3-(8':11'-pentadecadienyl)phenol and 3-(8:11:14'-pentadecatrienyl)phenol. Formulae presented in both the '092 and '708 patents as well as the chemical literature (see the Dictionary of Organic Compounds, Vol. 1, Oxford University Press, N.Y., 1965, page 229) show that the C$_{15}$ substituent in cardanol is meta to the hydroxy group.

U.S. Pat. No. 2,859,251 discloses the alkylation of ortho-, para-, and meta-amino phenols with olefin polymers having from 6 to 18 carbon atoms per molecule in the presence of a catalytic complex formed by mixing hydrogen fluoride with boron trifluoride and an iron group metal fluoride. The '251 patent fails to disclose whether the alkyl groups in the product mixture are bonded to carbon, nitrogen, and/or oxygen atom.

GENERAL BACKGROUND

The improvement of the performance characteristics of lubricants based on oils of lubricating viscosity (e.g., oils and greases) and normally liquid fuels through the use of additives has been known for several decades. Still, in these days of growing material shortages, spiralling equipment replacement costs, increasing fuel and lubricant costs, and environmental consciousness, the search for new, effective, alternate lubricant and fuel additives continues unabated.

OBJECTS

Therefore, it is an object of this invention to provide novel additive compositions that will impart useful and desirable properties to oil-based lubricants and normally liquid fuels containing said additive compositions.

It is a further object of this invention to provide novel concentrates and lubricants and fuels containing the amino phenols of this invention.

Other objects will be apparent to those skilled in the art upon review of the present specification.

SUMMARY OF THE INVENTION

This invention comprises amino phenols of the formula

Formula I wherein R is a substantially saturated hydrocarbon-based substituent of at least 30 aliphatic carbon atoms; a, b, and c are each independently an integer of 1 up to three times the number of aromatic nuclei present in Ar with the proviso that the sum of a, b, and c does not exceed the unsatisfied valences of Ar; and Ar is an aromatic moiety having 0 to 3 optional substituents selected from the group consisting of lower alkyl, lower alkoxyl, nitro, halo, or combinations of two or more of said optional substituents; with the proviso that when Ar is a benzene nucleus having only one hydroxyl and one R substituent, the R substituent is ortho or para to said hydroxyl substituent.

The term "phenol" is used in this specification in its art-accepted generic sense to refer to hydroxy-aromatic compounds having at least one hydroxyl group bonded directly to a carbon of an aromatic ring.

Lubricants based on oils of lubricating viscosity, normally liquid fuels and additive concentrates containing the above-described amino phenols are also embodiments of this invention.

DESCRIPTION OF THE INVENTION

The aromatic moiety, Ar

The aromatic moiety, Ar, can be a single aromatic nucleus such as a benzene nucleus, a pyridine nucleus, a thiophene nucleus, a 1,2,3,4-tetrahydronaphthalene nucleus, etc., or a polynuclear aromatic moiety. Such polynuclear moieties can be of the fused type; that is, wherein at least two aromatic nuclei are fused at two points to another nucleus such as found in naphthalene, anthracene, the azanaphthalenes, etc. Such polynuclear aromatic moieties also can be of the linked type wherein at least two nuclei (either mono or polynuclear) are linked through bridging linkages to each other. Such bridging linkages can be chosen from the group consisting of carbon-to-carbon single bonds, ether linkages, keto linkages, sulfide linkages, polysulfide linkages of 2 to 6 sulfur atoms, sulfinyl linkages, sulfonyl linkages, methylene linkages, alkylene linkages, di-(lower alkyl)-methylene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between aromatic nuclei. For example, a fluorene nucleus has two benzne nuclei linked by both a methylene linkage and a covalent band. Such a nucleus may be considered to have 3 nuclei but only two of them are aromatic. Normally, Ar will contain only carbon atoms in the aromatic nuclei per se.

The number of aromatic nuclei, fused, linked or both, in Ar can play a role in determining the integer values of a, b and c in Formula I. For example, when Ar contains a single aromatic nucleus, a, b and c are each independently 1 to 3. When Ar contains 2 aromatic nuclei, a, b and c can each be an integer of 1 to 6, that is, up to three times the number of aromatic nuclei present (in naphthalene, 2). With a trinuclear Ar moiety a, b and c can each be an integer of 1 to 9. For example, when Ar is a biphenyl moiety, a, b and c can each independently be an integer of 1 to 6. The values of a, b and c are obviously limited by the fact that their sum cannot exceed the total unsatisfied valences of Ar.

The single ring aromatic nucleus which can be the Ar moiety can be represented by the general formula ar(Q)$_m$ wherein ar represents a single ring aromatic nucleus (e.g., benzene) of 4 to 10 carbons, each Q independently represents a lower alkyl group, lower alkoxy group, nitro group, or halogen atom, and m is 0 to 3. As used in this specification and appended claims, "lower" refers to groups having 7 or less carbon atoms such as lower alkyl and lower alkoxyl groups. Halogen atoms include fluorine, chlorine, bromine and iodine atoms; usually, the halogen atoms are fluorine and chlorine atoms.

Specific examples of such single ring Ar moieties are the following:

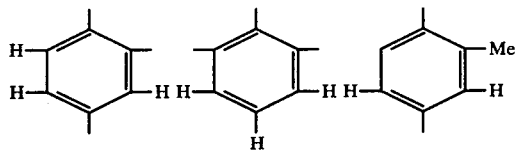

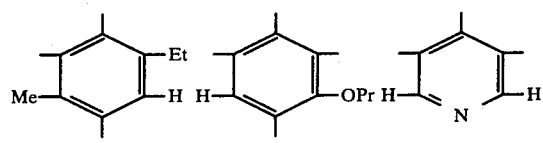

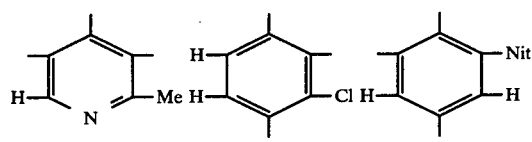

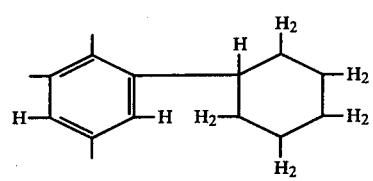

-continued

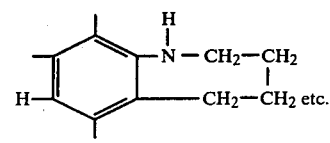

wherein Me is methyl, Et is ethyl, Pr is n-propyl, and Nit is nitro.

When Ar is a polynuclear fused-ring aromatic moiety, it can be represented by the general formula ar$\{$ar$\}_{m'}$ (Q)$_{mm'}$ wherein ar, Q and m are as defined hereinabove, m' is 1 to 4 and ⊃ represent a pair of fusing bonds fusing two rings so as to make two carbon atoms part of the rings of each of two adjacent rings. Specific examples of fused ring aromatic moieties Ar are:

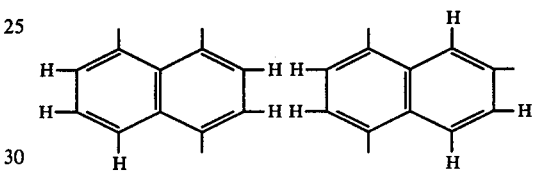

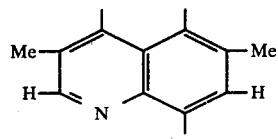

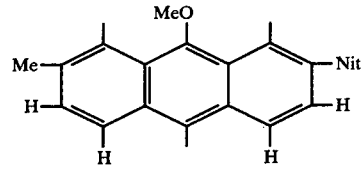

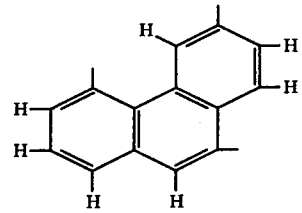

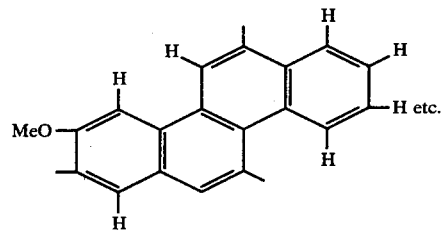

When the aromatic moiety Ar is a linked polynuclear aromatic moiety it can be represented by the general formula ar—(Lng-ar)$_w$—(Q)$_{mw}$ wherein w is an integer of 1 to about 20, ar is as described above with the proviso that there are at least 3 unsatisfied (i.e., free) valences in the total of ar groups, Q and m are as defined hereinbefore, and each Lng is a bridging linkage individually chosen from the group consisting of carbon-to-carbon single bonds, ether linkages (e.g., —O—), keto linkages

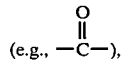

sulfide linkages (e.g., —S—), polysulfide linkages of 2 to 6 sulfur atoms (e.g., —S$_{2-6}$—), sulfinyl linkages (e.g., —S(O)—), sulfonyl linkages (e.g., —S(O)$_2$—), lower alkylene linkages (e.g., —CH$_2$—, —CH$_2$—CH$_2$—,

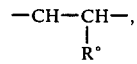

etc.), di(lower alkyl)methylene linkages (e.g., —CR$_2^o$—), lower alkylene ether linkages (e.g., —CH$_2$O—, —CH$_2$O—CH$_2$—, —CH$_2$—CH$_2$O—, —CH$_2$CH$_2$OCH$_2$CH$_2$—,

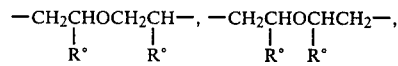

etc.), lower alkylene keto linkages

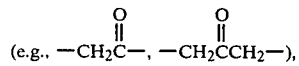

lower alkylene sulfide linkages (e.g., wherein one or more —O—'s in the lower alkylene ether linkages is replaced with an —S— atom), lower alkylene polysulfide linkages (e.g., wherein one or more —O—'s is replaced with a —S$_{2-6}$ group), amino linkages e.g.,

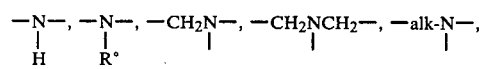

where alk is lower alkylene, etc.), polyamino linkages (e.g.,

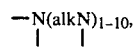

where the unsatisfied free N valences are taken up with H atoms or R° groups), and mixtures of such bridging linkages (each R° being a lower alkyl group).

Specific examples of Ar when it is a linked polynuclear aromatic moiety include:

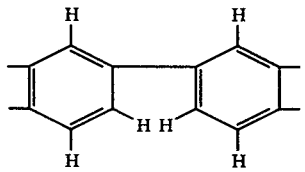

-continued

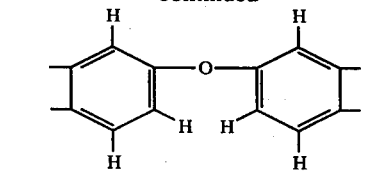

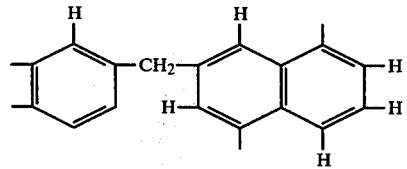

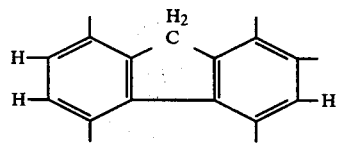

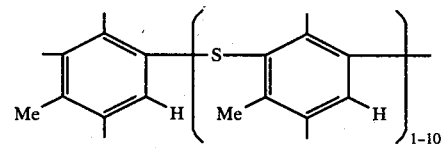

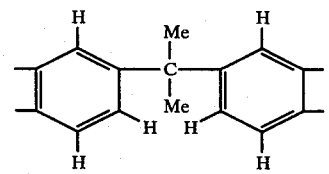

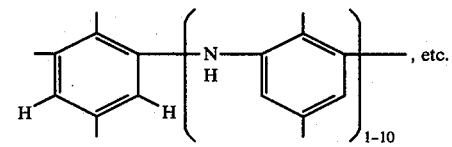

Usually all these Ar moieties are unsubstituted except for the R, —OH and —NH$_2$ groups (and any bridging groups).

In many instances the Ar moieties are of the class Ar* which consists of single ring aromatic moieties (e.g., benzene, toluene, thiophene, pyridine, etc.) and fused ring moieties (e.g., naphthalene, phenanthrene, azanaphthalene, etc.). All the foregoing disclosures relating to single and fused ring moieties within the class Ar apply equally to the class Ar*. Only the afore-described linked ring moieties are not part of the class Ar*.

Often, when the aromatic moiety is Ar or Ar*, a, b and c are 1 and there are zero optional substituents.

For such reasons as cost, availability, performance, etc., the Ar moiety is normally a benzene nucleus, lower alkylene bridged benzene nucleus, or a naphthalene nucleus. Thus, a typical Ar moiety is a benzene or naphthalene nucleus having 3 to 5 unsatisfied valences, so that one or two of said valences may be satisfied by a hydroxyl group with the remaining unsatisfied valences being, insofar as possible, either ortho or para to a hydroxyl group. Preferably, Ar is a benzene nucleus having 3 to 4 unsatisfied valences so that one can be satisfied by a hydroxyl group with the remaining 2 or 3 being either ortho or para to the hydroxyl group.

The Substantially Saturated Hydrocarbon-Based Group R

The amino phenols of the present invention contain, directly bonded to the aromatic moiety Ar, a substantially saturated monovalent hydrocarbon-based group R of at least about 30 aliphatic carbon atoms. This R group can have up to about 750 aliphatic carbon atoms. Usually it has a maximum of about 400 carbon atoms. In some instances R has a minimum of about 50 carbon atoms. More than one such group can be present, but usually, no more than 2 or 3 such groups are present for each aromatic nucleus in the aromatic moiety Ar. The total number of R groups present in indicated by the value for "a" in Formula I. Usually, the hydrocarbon-based group has at least about 30, more typically, at least about 50 aliphatic carbon atoms and up to about 750, more typically, up to about 400, sometimes up to about 300 aliphatic carbon atoms.

Generally, the hydrocarbon-based groups R are made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, 1-octene, etc. Typically, these olefins are 1-monoolefins. The R groups can also be derived from the halogenated (e.g., chlorinated or brominated) analogs of such homo- or interpolymers. The R groups can, however, be made from other sources, such as monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. Any unsaturation in the R groups may be reduced or eliminated by hydrogenation according to procedures known in the art before the nitration step described hereafter.

As used herein, the term "hydrocarbon-based" denotes a group having a carbon atom directly attached to the remainder of the molecule and having a predominantly hydrocarbon character within the context of this invention. Therefore, hydrocarbon-based groups can contain up to one non-hydrocarbon radical for every ten carbon atoms provided this non-hydrocarbon radical does not significantly alter the predominantly hydrocarbon character of the group. Those skilled in the art will be aware of such radicals, which include, for example, hydroxyl, halo (especially chloro and fluoro), alkoxyl, alkyl mercapto, alkyl sulfoxy, etc. Usually, however, the hydrocarbon-based groups R are purely hydrocarbyl and contain no such non-hydrocarbyl radicals.

The hydrocarbon-based groups R are substantially saturated, that is, they contain no more than one carbon-to-carbon unsaturated bond for every ten carbon-to-carbon single bonds present. Usually, they contain no more than one carbon-to-carbon non-aromatic unsaturated bond for every 50 carbon-to-carbon bonds present.

The hydrocarbon-based groups of the amino phenols of this invention are also substantially aliphatic in nature, that is, they contain no more than one non-aliphatic moiety (cycloalkyl, cycloalkenyl or aromatic) group of six or less carbon atoms for every ten carbon atoms in the R group. Usually, however, the R groups contain no more than one such non-aliphatic group for every fifty carbon atoms, and in many cases, they contain no such non-aliphatic groups at all; that is, the typical R groups are purely aliphatic. Typically, these purely aliphatic R groups are alkyl or alkenyl groups.

Specific examples of the substantially saturated hydrocarbon-based R groups are the following:

a tetracontanyl group a henpentacontanyl group a mixture of poly(ethylene/propylene) groups of about 35 to about 70 carbon atoms a mixture of the oxidatively or mechanically degraded poly(ethylene/propylene) groups of about 35 to about 70 carbon atoms a mixture of poly(propylene/1-hexene) groups of about 80 to about 150 carbon atoms a mixture of poly(isobutene) groups having between 20 and 32 carbon atoms a mixture of poly(isobutene) groups having an average of 50 to 75 carbon atoms A preferred source of the group R are poly(isobutene)s obtained by polymerization of a C₄ refinery stream having a butene content of 35 to 75 weight percent and isobutene content of 30 to 60 weight percent in the presence of a Lewis acid catalyst such as aluminum trichloride or boron trifluoride. These polybutenes contain predominantly (greater than 80% of total repeat units) isobutene repeating units of the configuration

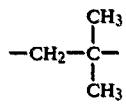

The attachment of the hydrocarbon-based group R to the aromatic moiety Ar of the amino phenols of this invention can be accomplished by a number of techniques well known to those skilled in the art. One particularly suitable technique is the Friedel-Crafts reaction, wherein an olefin (e.g., a polymer containing an olefinic bond), or halogenated or hydrohalogenated analog thereof, is reacted with a phenol. The reaction occurs in the presence of a Lewis acid catalyst (e.g., boron trifluoride and its complexes with ethers, phenols, hydrogen fluoride, etc., aluminum chloride, aluminum bromide, zinc dichloride, etc.). Methods and conditions for carrying out such reactions are well known to those skilled in the art. See, for example, the discussion in the article entitled, "Alkylation of Phenols" in "Kirk-Othmer Encyclopedia of Chemical Technology", Second Edition, Vol. 1, pages 894-895, Interscience Publishers, a division of John Wiley and Company, New York, 1963. Other equally appropriate and convenient techniques for attaching the hydrocarbon-based group R to the aromatic moiety Ar will occur readily to those skilled in the art.

As will be appreciated from inspection of Formula I that the amino phenols of this invention contain at least one of each of the following substituents: a hydroxyl group, a R group as defined above, and a primary amine group, $-NH_2$. Each of the foregoing groups must be attached to a carbon atom which is a part of an aromatic nucleus in the Ar moiety. They need not, however, each be attached to the same aromatic ring if more than one aromatic nucleus is present in the Ar moiety.

In a preferred embodiment, the amino phenols of this invention contain one each of the foregoing substituents and but a single aromatic ring, most preferably benzene. This preferred class of amino phenols can be represented by the formula

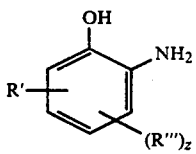

Formula IIA wherein the R' group is a hydrocarbon-based group of about 30 to about 400 aliphatic carbon atoms located ortho or para to the hydroxyl group, R''' is a lower alkyl, lower alkoxyl, nitro group or halogen atom and z is 0 or 1. Usually z is 0 and R' is a substantially saturated, purely aliphatic group. Often it is an alkyl or alkenyl group para to the —OH substituent.

In another preferred embodiment, the amino phenols of this invention can be represented by the formula

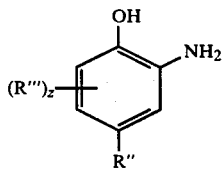

Formula IIB wherein R* is a substantially saturated hydrocarbon-based group having an average of from about 30 to about 750 aliphatic carbon atoms and R''' is as defined above.

In a still more preferred embodiment of this invention, the amino phenol is of the formula

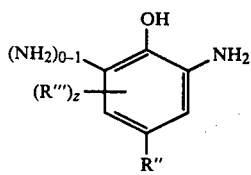

Formula IIIA wherein R'' is derived from homopolymerized or interpolymerized $C_{2-10}$ 1-olefins and has an average of from about 30 to about 300 aliphatic carbon atoms and R''' and z are as defined above. Usually R'' is derived from ethylene, propylene, butylene and mixtures thereof. Typically, it is derived from polymerized isobutene. Often R'' has at least about 50 aliphatic carbon atoms and z is 0.

In another aspect of the preferred embodiments of this invention, the amino phenols can be represented by the formula

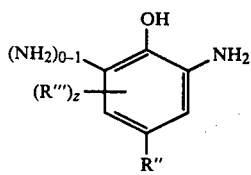

Formula IIIB wherein R''', R'' and z are as defined above. When only one —NH₂ group is present in the amino phenols represented in Formulae IIB and IIIB, R''', if present (i.e., z≠0), can be ortho to the phenolic —OH group.

The amino phenols of the present invention can be prepared by a number of synthetic routes. These routes can vary in the type reactions used and the sequence in which they are employed. For example, an aromatic hydrocarbon, such as benzene, can be alkylated with alkylating agent such as a polymeric olefin to form an alkylated aromatic intermediate. This intermediate can then be nitrated, for example, to form polynitro intermediate. The polynitro intermediate can in turn be reduced to a diamine, which can then be diazotized and reacted with water to convert one of the amino groups into a hydroxyl group and provide the desired amino phenol. Alternatively, one of the nitro groups in the polynitro intermediate can be converted to a hydroxyl group through fusion with caustic to provide a hydroxy-nitro alkylated aromatic which can then be reduced to provide the desired amino phenol.

Another useful route to the amino phenols of this invention involves the alkylation of a phenol with an olefinic alkylating agent to form an alkylated phenol. This alkylated phenol can then be nitrated to form an intermediate nitro phenol which can be converted to the desired amino phenols and by reducing at least some of the nitro groups to amino groups.

Techniques for alkylating phenols are well known to those skilled in the art as the above-noted article in Kirk-Othmer "Encyclopedia of Chemical Technology" demonstrates. Techniques for nitrating phenols are also known. See, for example, in Kirk-Othmer "Encyclopedia of Chemical Technology", Second Edition, Vol. 13, the article entitled "Nitrophenols", page 888 et seq., as well as the treatises "Aromatic Substitution; Nitration and Halogenation" by P. B. D. De La Mare and J. H. Ridd, New York, Academic Press, 1959; "Nitration and Aromatic Reactivity" by J. G. Hogget, London, Cambridge University Press, 1961; and "The Chemistry of the Nitro and Nitroso Groups", Henry Feuer, Editor, Interscience Publishers, New York, 1969.

Aromatic hydroxy compounds can be nitrated with nitric acid, mixtures of nitric acid with acids such as sulfuric acid or boron trifluoride, nitrogen tetraoxide, nitronium tetrafluoroborates and acyl nitrates. Generally, nitric acid of a concentration of, for example, about 60–90% is a convenient nitrating reagent. Substantially inert liquid diluents and solvents such as acetic or butyric acid can aid in carrying out the reaction by improving reagent contact.

Conditions and concentrations for nitrating hydroxy aromatic compounds are also well known in the art. For example, the reaction can be carried out at temperatures of about −15° C. to about 150° C. Usually nitration is conveniently carried out between about 25°–75° C.

Generally, depending on the particular nitrating agent about 0.5–4 moles of nitrating agent is used for every mole of aromatic nucleus present in the hydroxy aromatic intermediate to be nitrated. If more than one aromatic nucleus is present in the Ar moiety, the amount of nitrating agent can be increased proportionately according to the number of such nuclei present. For example, a mole of naphthalene-based aromatic intermediate has, for purposes of this invention, the equivalent of two "single ring" aromatic nuclei so that about 1–4 moles of nitrating agent would generally be used. When nitric acid is used as a nitrating agent usually about 1.0 to about 3.0 moles per mole of aromatic nucleus is used. Up to about a 5-molar excess of nitrating agent (per "single ring" aromatic nucleus) may be used when it is desired to drive the reaction forward or carry it out rapidly.

Nitration of a hydroxy aromatic intermediate generally takes 0.25 to 24 hours, though it may be convenient to react the nitration mixture for longer periods, such as 96 hours.

Reduction of aromatic nitro compounds to the corresponding amines is also well known. See, for example, the article entitled "Amination by Reduction" in Kirk-Othmer "Encyclopedia of Chemical Technology", Second Edition, Vol. 2, pages 76–99. Generally, such reductions can be carried out with, for example, hydrogen, carbon monoxide or hydrazine, (or mixtures of same) in the presence of metallic catalysts such as palladium, platinum and its oxides, nickel, copper chromite, etc. Co-catalysts such as alkali or alkaline earth metal hydroxides or amines (including amino phenols) can be used in these catalyzed reductions.

Reduction can also be accomplished through the use of reducin metals in the presence of acids, such as hydrochloric acid. Typical reducing metals are zinc, iron and tin; salts of these metals can also be used.

Nitro groups can also be reduced in the Zinin reaction, which is discussed in "Organic Reactions", Vol. 20, John Wiley & Sons, New York, 1973, page 455 et seq. Generally, the Zinin reaction involves reduction of a nitro group with divalent negative sulfur compounds, such as alkali metal sulfides, polysulfides and hydrosulfides.

The nitro groups can be reduced by electrolytic action; see, for example, the "Amination by Reduction" article, referred to above.

Typically the amino phenols of this invention are obtained by reduction of nitro phenols with hydrogen in the presence of a metallic catalyst such as discussed above. This reduction is generally carried out at temperatures of about 15°–250° C., typically, about 50°–150° C., and hydrogen pressures of about 0–2000 psig, typically, about 50–250 psig. The reaction time for reduction usually varies between about 0.5–50 hours. Substantially inert liquid diluents and solvents, such as ethanol, cyclohexane, etc., can be used to facilitate the reaction. The amino phenol product is obtained by well-known techniques such as distillation, filtration, extraction, and so forth.

The reduction is carried out until at least about 50%, usually about 80%, of the nitro groups present in the nitro intermediate mixture are converted to amino groups. The typical route to the amino phenols of this invention just described can be summarized as (I) nitrating with at least one nitrating agent at least one compound of the formula

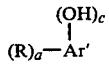

wherein R is a substantially saturated hydrocarbon-based group of at least 10 aliphatic carbon atoms; a and c are each independently an integer of 1 up to three times the number of aromatic nuclei present in Ar with the proviso that the sum of a, b and c does not exceed the unsatisfied valences of Ar'; and Ar' is an aromatic moiety having 0 to 3 optional substituents selected from the group consisting of lower alkyl, lower alkoxyl, nitro, and halo, or combinations of two or more optional substituents, with the provisos that (a) Ar' has at least one hydrogen atom directly bonded to a carbon atom which is part of an aromatic nucleus, and (b) when Ar' is a benzene having only one hydroxyl and one R substituent, the R substituent is ortho or para to said hydroxyl substituent, to form a first reaction mixture containing a nitro intermediate, and (II) reducing at least about 50% of the nitro groups in said first reaction mixture to amino groups.

Typically the Ar' moieties are of the Ar" type which consists of single ring aromatic moieties (e.g., benzene, toluene, thiophene, pyridine, etc.) and fused ring moieties (e.g., naphthalene, phenanthrene, azanaphthalene, etc.). All the foregoing preferences and discussion of Ar' apply where appropriate to the Ar" moieties.

Usually this means reducing at least about 50% of the nitro groups to amino groups in a compound or mixture of compounds of the formula

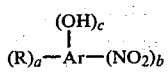

or

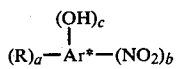

wherein R is a substantially saturated hydrocarbon-based substituent of at least 10 aliphatic carbon atoms; a, b and c are each independently an integer of 1 up to three times the number of aromatic nuclei present in Ar with the proviso that the sum of a, b and c does not exceed the unsatisfied valences of Ar or Ar*; and Ar and Ar* are as described hereinabove; with the proviso that when Ar or Ar* is a benzene nucleus having only one hydroxyl and one R substituent, the R substituent is ortho or para to said hydroxyl substituent.

The following examples demonstrate the practice of the present invention in some of its various aspects. All parts and percentages in the examples and elsewhere in the specification and claims are by weight and likewise, all temperatures are in degrees centrigrade (°C.), unless expressly stated to the contrary.

EXAMPLE 1A

To a mixture of 361.2 parts of a tetrapropenyl-substituted phenol and 270.9 parts of glacial acetic acid, at 7°–17°, is added a mixture of 90.3 parts of nitric acid (70–71% HNO$_3$) and 90.3 parts of glacial acetic acid. The addition is carried out over 1.5 hours while the reaction mixture is cooled externally to keep it at 7°–17°. The cooling bath is removed and the reaction stirred for 2 hours at room temperature. The reaction is then stripped at 134°/35 tor and filtered to provide the desired nitrated intermediate as a filtrate having a nitrogen content of 4.65%.

EXAMPLE 1B

A mixture of 150 parts of the product of 1A and 50 parts of ethanol is added to an autoclave. This mixture is degassed by purging with nitrogen and 0.75 part of palladium on charcoal catalyst is added. The autoclave is evacuated and pressured with nitrogen several times and then put under a hydrogen pressure of 100 psig. The reaction mixture is kept at 95° to 100° for 2.5 hours while the hydrogen pressure varies from 100 to 20 psig. As the hydrogen pressure drops below 30 psig, it is adjusted back to 100 psig. The reaction is continued for 20.5 hours at which point the autoclave is reopened and an additional 0.5 part of palladium on charcoal catalyst added. After repeated nitrogen purging (3 times) the autoclave is again pressured to 100 psig with hydrogen and the reaction continued for an additional 16.5 hours. A total of 1.63 moles of hydrogen is fed to the autoclave. The reaction mixture is filtered and stripped to 130°/16 tor. A second filtration provides the product which has the nitrogen content of 4.78%.

EXAMPLE 2A

To a mixture of 3,685 parts of a polyisobutene-substituted phenol (wherein the polyisobutene substituent contains 22 to 25 carbon atoms) and 1,400 parts of textile spirits is added 790 parts of nitric acid (70%). The reaction temperature is kept below 50°. After being stirred for about 0.7 hour, the reaction mixture is poured into 5,000 parts of ice and stored for 16 hours. The organic layer which separates is washed twice with water and then combined with 1,000 parts of benzene. This solution is stripped to 170° and the residue filtered to provide the desired intermediate having a nitrogen content of 2.41% and a viscosity at 99° of 150.8 SUS.

EXAMPLE 2B

A mixture of 130 parts of the product of 2A, 130 parts of ethanol, and 0.2 part of platinum oxide (PtO$_2$) is charged to a hydrogenation bomb. The bomb is purged several times with hydrogen and then charged to 54 psig with hydrogen. The bomb is rocked for 24 hours and again charged to 70 psig with hydrogen. Rocking is continued for an additional 98 hours. Stripping of the resulting reaction mixture to 145°/760 tor provides the desired product.

EXAMPLE 2C

A mixture of 420 parts of the product of 2A, 326 parts of ethanol and 12 parts of commercial nickel on kieselguhr catalyst is charged to an appropriately sized hydrogenation bomb. The bomb is pressured to 1,480 psig with hydrogen and agitated for 5.25 hours. The resultant reaction mixture is stripped to 65° C./30 tor to provide the product as a residue having a nitrogen content of 2.62%.

EXAMPLE 2D

A mixture of 105 parts of the product of 2A, 303 parts cyclohexane and 4 parts commercial Raney nickel catalyst is charged to an appropriately sized hydrogenation bomb. The bomb is pressured to 1,000 psig with hydrogen and agitated at about 50° for 16 hours. The bomb is again pressured to 1,100 psig and agitated for another 24 hours. The bomb is then opened and the reaction mixture filtered and recharged to the bomb with a fresh portion of 4 parts of Raney nickel catalyst. The bomb is pressured to 1,100 psig and agitated for 24 hours. The resultant reaction mixture is stripped to 95°/28 tor to provide the product having a hydroxyl content of 5.24% and a nitrogen content of 2.25%.

EXAMPLE 3A

An alkylated phenol is prepared by reacting phenol with polyisobutene having a number average molecular weight of approximately 1000 (vapor phase osmometry) in the presence of a boron trifluoride phenol complex catalyst. Stripping of the product thus formed first to 230°/760 tor (vapor temperature) and then to 205° vapor temperature/50 tor provides purified alkylated phenol.

To a mixture of 265 parts of purified alkyl phenol, 176 parts blend oil and 42 parts of a petroleum naphtha having a boiling point of approximately 20° is added slowly to a mixture of 18.4 parts of concentrated nitric acid (69–70%) and 35 parts of water. The reaction mixture is stirred for 3 hours at about 30°–45°, stripped to 120°/20 tor and filtered to provide an oil solution of the desired nitro phenol intermediate.

EXAMPLE 3B

A mixture of 1,500 parts of the product solution of 3A, 642 parts of isopropanol and 7.5 parts of nickel on kieselguhr catalyst is charged to an autoclave under a nitrogen atmosphere. After purging and evacuation with nitrogen 3 times, the autoclave is pressured to 100 psig with hydrogen and stirring is begun. The reaction mixture is held at 96° for a total of 14.5 hours while a total of 1.66 moles of hydrogen is fed to it. After purging with nitrogen 3 times the reaction mixture is filtered and the filtrate stripped to 120°/18 tor. Filtration provides the desired product in an oil solution containing 0.54% nitrogen.

EXAMPLE 4A

To a mixture of 400 parts of polyisobutene-substituted phenol (wherein the polyisobutene substituent contains approximately 100 carbon atoms), 125 parts of textile spirits and 266 parts of a diluent mineral oil at 28° is slowly added 22.83 parts of nitric acid (70%) in 50 parts of water over a period of 0.33 hour. The mixture is stirred at 28°–34° for 2 hours and stripped to 158°/30 tor, filtration provides an oil solution (40%) of the desired intermediate having a nitrogen content of 0.88%.

EXAMPLE 4B

A mixture of 93 parts of the product solution of Example 4A and 93 parts of a mixture of toluene and isopropanol (50/50 by weight) is charged to an appropriately sized hydrogenation vessel. The mixture is degassed and nitrogen purged; 0.31 part of a commercial platinum oxide catalyst (86.4% PtO$_2$) is added. The reaction vessel is pressured to 57 psig and held at 50°–60° for 21 hours. A total of 0.6 mole of hydrogen is fed to the reaction vessel. The reaction mixture is then filtered and the filtrate stripped to yield the desired product in an oil solution containing 0.44% nitrogen.

EXAMPLE 5A

A mixture of 2,160 parts of the polyisobutene-substituted phenol of Example 4A and 1,440 parts of a diluent mineral oil is heated to 60°. Then 25 parts of paraformaldehyde is added to the mixture followed by 15 parts of aqueous hydrochloric acid. The mixture is heated to 115° for 1 hour. After storage for 16 hours at room temperature the reaction mixture is heated to 160° for 1 hour while 20 parts of distillate are removed. Stripping of the reaction mixture to 160°/15 tor provides an oil solution of the desired methylene-linked, polyisobutene-substituted phenol.

EXAMPLE 5B

To 2,406 parts of the oil solution described in Example 5A and 600 parts of textile spirits is added 90 parts nitric acid (70%) over 1.5 hours. The reaction mixture is stirred for 1.5 hours, stored for 63 hours at room temperature and then heated for 8 hours at 90°. Stripping to 160°/18 tor provides an oil solution of the desired nitrated intermediate containing 0.79% nitrogen.

EXAMPLE 5C

A mixture of 800 parts of the oil solution of Example 5B and 720 parts of a toluene/isopropyl mixture (60/40 by weight) is charged to an autoclave. After nitrogen purging, 4 parts of nickel on kieselguhr catalyst is added. Nitrogen purging is repeated 3 times and the autoclave pressured with hydrogen to 60 psig at 25°. The reaction temperature is slowly increased to 96° and the pressure maintained at 100 psig for 5.5 hours. The autoclave is then opened and an additional 4 parts of nickel on kieselguhr catalyst added. The autoclave is repressured to 100 psig hydrogen and held at 96° and 100 psig for 6 hours. The autoclave is cooled and reopened; an additional 0.8 part of platinum oxide catalyst added. The autoclave is then repressured to 90 psig with hydrogen and kept at this pressure for 8 more hours. The reaction mixture is filtered and the filtrate stripped to 150°/18 tor to provide an oil solution of the product having a nitrogen content of 0.41%.

EXAMPLE 6A

A mixture of 1,962 parts of the polyisobutene-substituted phenol of Example 3A, 49.5 parts of paraformaldehyde, 15 parts of aqueous hydrochloric acid and 1,372 parts of diluent mineral oil is heated for 7 hours at 115°. The reaction temperature is then increased to 160°–165° and held there for an additional 7 hours. Four hundred parts of textile spirits is added to the mixture and it is cooled to 30°. Then 136.95 parts of nitric acid (70%) in 140 parts of water is slowly added. The reaction mixture is stirred for 1.5 hours at 30°–35° and then stripped to 170°/28 tor to provide an oil solution of the intermediate which is clarified by filtration.

EXAMPLE 6B

Ninety-six parts of the oil solution described in Example 6A and 96 parts of a toluene/isopropyl alcohol mixture (50/50 by weight) is charged to an appropriately sized hydrogenation vessel. After nitrogen purging 0.32 part of platinum oxide catalyst is added. After again purging the reaction vessel, it was pressured to 157 psig at 25° with hydrogen. The hydrogen pressure is kept between 57 and 50 psig for 60 hours while reaction mixture is heated to 50° to 60°. The resultant reaction mixture is filtered and stripped to provide an oil solution of the product having a nitrogen content of 0.353%.

EXAMPLE 7A

To a mixture of 654 parts of the polyisobutene-substituted phenol of Example 3A and 654 parts of isobutyric acid at 27° to 31°, is added 90 parts of 16 molar nitric acid over a period of 0.5 hour. The reaction mixture is held at 50° for 3 hours and then stored at room temperature for 63 hours. Stripping to 160°/26 tor and filtration through filter aid provides the desired nitro intermediate which has a nitrogen content of 1.8%.

EXAMPLE 7B

The nitro product of Example 7A is hydrogenated using a nickel on kieselguhr catalyst following essentially the same procedure described in Example 3B.

EXAMPLE 8A

A mixture of 4,578 parts of the polyisobutene-substituted phenol of Example 3A, 3,052 parts of diluent mineral oil and 725 parts of textile spirits is heated to 60° to achieve homogenity. After cooling to 30°, 319.5 parts of 16 molar nitric acid in 600 parts of water is added to the mixture. Cooling is necessary to keep the mixture below 40°. After stirring the reaction mixture for an additional 2 hours, 3,710 parts is transferred to a second reaction vessel. This 3710 parts is treated with an additional 127.82 parts of 16 molar nitric acid in 130 parts of water at 25°–30°. The reaction mixture is stirred for 1.5 hours and then stripped to 220°/30 tor. Filtration provides an oil solution of the intermediate.

EXAMPLE 8B

The oil solution of the product formed in Example 8A is hydrogenated using a platinum oxide catalyst in substantially the same fashion as described in Example 2B to provide a diamino phenol.

EXAMPLE 9

A mixture of 543 parts of a dinitro $C_{25}$-alkylated phenol (prepared in essentially the same manner as described in Example 8B), 543 parts of isopropanol and 200 parts of toluene is treated at 19° C. with a total of 42 parts of gaseous ammonia over a 0.75 hour period. The reaction mixture is then treated with 147 parts of gaseous $H_2S$. Both the ammonia and hydrogen sulfide treatment are carried out by introducing the gas into the stirred mixture under its surface. Ammonia treatment is repeated with 82 parts of gaseous ammonia followed by a final treatment with 102 parts of hydrogen sulfide. Stripping of the reaction mixture to 40°/60 tor yields a residue which is combined with 161 parts of diluent oil and stripped again to 70° C./18 torr. An additional 161 parts of diluent oil and 35 parts of filter aid are added; filtration of this mixture yields a viscous filtrate which is a 40% oil solution of the desired diamino phenol.

The nitrations in examples 10–16 are carried out in essentially the same manner described in Example 1A, using the hydroxy aromatic compounds and amounts of nitric acid indicated in Table A. Reduction of the nitro intermediates in these examples is carried out using the technique described in the examples indicated in Table A.

TABLE A

| EXAMPLE | HYDROXY AROMATIC COMPOUND | | MOLES $HNO_3$[2] | REDUCTION TECHNIQUE[3] |
|---|---|---|---|---|
| | Name | Mol. Wt.[1] | | |
| 10 | 2,2'-dipoly(isobutene)yl-4,4'-dihydroxy biphenyl | 2500 | 2.2 | 3B |
| 11 | 8-hydroxy-?-poly(propene)yl-1-azanaphthalene | 900 | 1.0 | 9 |
| 12 | 4-poly(isobutene)yl-1-naphthol | 1700 | 1.1 | 3B |
| 13 | 2-poly(propene/butene-1)yl-4,4'-isopropylidene-bisphenol[4] | 3200 | 2.4 | 1B |
| 14 | 4-tetra(propene)yl-2-hydroxyanthracene | — | 1.0 | 9 |
| 15 | 4-octadecyl-1,3-dihydroxybenzene | — | 2.2 | 1B |

TABLE A-continued

| | HYDROXY AROMATIC COMPOUND | | | REDUCTION |
|---|---|---|---|---|
| EXAMPLE | Name | Mol. Wt.[1] | MOLES HNO$_3$[2] | TECHNIQUE[3] |
| 16 | 4-poly(isobutene)-3-hydroxy pyridine | 1300 | 1.0 | 9 |

[1] Number average molecular weight by vapor phase osmometry
[2] Moles of HNO$_3$ per mole of "single ring" aromatic nucleus
[3] I.e., essentially the same technique described in the indicated example
[4] The molar ratio of propene to butene-1 in the substituent is 2:3

EXAMPLE 17

To a mixture of 1,056 parts of tetrapropyl-substituted phenol and 792 parts acetic acid cooled to −9° is added a mixture of 282 parts concentrated nitric acid and 264 parts acetic acid. The reaction mixture is stirred at 8°-27° for 5 hours; external cooling is required to keep the reaction temperature within this range. The reaction mixture is stripped to 132°/36 tor and the residue filtered to provide the desired nitro intermediate.

EXAMPLE 17B

To a mixture of 680 parts of the intermediate described in Example 17A, 340 parts of denatured ethanol and 100 parts of water is quickly added 423 parts of commercial sodium sulfide. The cooling bath is used to keep the reaction temperature below about 65°. After stirring for approximately 1 hour, the reaction mixture is refluxed for 4 hours. The reaction mixture is then blown with carbon dioxide at 45°-30° for 3 hours; 500 parts of petroleum naphtha is added to the mixture and it is stirred for 16 hours. After addition of 500 parts of toluene, the reaction mixture is extracted with 500 parts of water. This extraction is repeated 4 times and the combined water extracts back-extracted with a mixture of petroleum naptha and toluene. The organic extracts are combined and stripped to provide a residue which is combined with 409 parts of blend oil. The combined mixture is then stripped to 105°/15 tor to provide an oil solution of the desired amino phenol.

As previously indicated, the amino phenols of this invention are useful as additives in preparing lubricant compositions where they function primarily as detergents and dispersants. They are particularly useful where the oil is subjected to high temperature environments or to cyclic stresses such as those encountered in on-and-off engine operation.

The lubricating oil compositions of this invention are based on natural and synthetic lubricating oils and mixtures thereof. These lubricants include crankcase lubricating oils for spark-ignited and compression-ignited internal combustion engines, such as automobile and truck engines, marine and railroad diesel engines, and the like. Automatic transmission fluids, transaxle lubricants, gear lubricants, metal-working lubricants, hydraulic fluids and other lubricating oil and grease compositions can also benefit from the incorporation therein of the amino phenols of the present invention.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide homopolymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500-1000, diethyl ether of polypropylene glycol having a molecular weight of 1000-1500, etc.) or mono- and polycarboxylic esters thereof, for example, the acetic acid esters, mixed $C_3$-$C_8$ fatty acid esters, or the $C_{13}$Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, secondary distillation, acid or base extraction, filtration, percolation, etc. Rerefined oils are obtained by processes, similar to those used to obtain refined oils, applied to refined oils which have been already used in service. Such rerefined oils are also known as reclaimed or reprocessed oils and often are additionally processed by techniques directed to removal of spent additives and oil breakdown products.

In general, about 0.05–30, usually about 0.1–15 parts (by weight) of at least one amino phenol of this invention is dissolved or stably dispersed in 100 parts of oil to produce a satisfactory lubricant. The invention also contemplates the use of other additives in combination with the composition of this invention. Such additives include, for example, auxiliary detergents and dispersants of the ash-producing or ashless type, oxidation-inhibiting agents, pour point depressing agents, extreme pressure agents, color stabilizers and anti-foam agents.

The amino phenols of this invention can also be used in fuels where they function as detergent dispersants, anti-oxidants and anti-corrosion agents. Fuel compositions of this invention usually contain a major portion of a normally liquid fuel such as hydrocarbonaceous petroleum distillate fuel (e.g., motor gasoline as defined by ASTM Specification D-439-73 and diesel fuel or fuel oil as defined by ASTM Specification D-396). Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Generally, these fuel compositions contain an amount of at least one amino phenol of this invention sufficient to impart anti-oxidant and/or dispersant and detergent properties to the fuel; usually this amount is about 1 to about 10,000, preferably 4 to 1,000, parts by weight of the reaction product per million parts by weight of fuel. The preferred gasoline-based fuel compositions generally exhibit excellent engine oil sludge dispersancy and detergency properties. In addition, they resist oxidation.

The fuel compositions of this invention can contain, in addition to the compositions of this invention, other additives which are well known to those of skill in the art. These can include anti-knock agents such as tetraalkyl lead compounds, lead scavengers such as haloalkanes (e.g., ethylene dichloride and ethylene dibromide), deposit preventors or modifiers such as triaryl phosphates, dyes, cetane improvers, anti-oxidants such as 2,6-di-tertiarybutyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described compositions of this invention are combined with other ashless dispersants in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Pat. No. 1,396,645, British Pat. Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification No. 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0; preferably about 1 to about 10 parts of composition of this invention to 1 part ashless dispersant.

The amino phenols of this invention can be added directly to the fuel or lubricating oil to form the fuel and lubricant compositions of this invention or they can be diluted with at least one substantially inert, normally liquid organic solvent/diluent such as mineral oil, xylene, or a normally liquid fuel as described above, to form an additive package which is then added to the fuel or lubricating oil in sufficient amounts to form the inventive fuel and lubricant composition described herein. These concentrates generally contain about 30 to about 90 percent of the composition of this invention and can contain, in addition, any of the above-described conventional additives, particularly the afore-described ashless dispersants in the aforesaid proportions. The remainder of the concentrate is the solvent/diluent.

What is claimed is:
1. A composition comprising a combination of:
(A) at least one amino phenol of the general formula

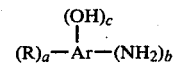

wherein R is a substantially saturated, hydrocarbon-based substituent of at least 30 aliphatic carbon atoms; a, b and c are each independently an integer of one up to three times the number of aromatic nuclei present in Ar with the proviso that the sum of a, b and c does not exceed the unsatisfied valences of Ar; and Ar is an aromatic moiety having 0–3 optional substituents selected from the group consisting of lower alkyl, lower alkoxyl, nitro, halo or combinations of two or more of said substituents; and
(B) at least one ashless dispersant, wherein said dispersant is an ester composition of a high molecular weight carboxylic acid acylating agent containing at least 30 carbon atoms in the acyl moiety wherein the weight ratios of (A) to (B) is about 0.1 to about 10 to 1.

2. A composition as claimed in claim 1 wherein R contains up to about 750 carbon atoms and there are no optional substituents attached to Ar.

3. A composition as claimed in claim 2 wherein R is an alkyl or alkenyl group.

4. A composition as claimed in claim 1 wherein R contains from about 50 to about 750 aliphatic carbon atoms and is made from a homo- or interpolymer of mono- and diolefins having 2 to 10 carbon atoms.

5. A composition as claimed in claim 4 wherein said olefins are selected from the group consisting of ethylene, propylene, butylene and mixtures thereof.

6. A composition as claimed in claim 1 wherein a, b and c are each 1, there are zero optional substituents attached to Ar, and Ar is a benzene nucleus.

7. A composition as claimed in claim 6 wherein R is an alkyl or alkenyl group of at least about 50 carbon atoms and up to about 750 carbon atoms and is derived from a homo- or interpolymer of 1-monoolefins having 2 to 10 carbon atoms.

8. A composition as claimed in claim 1 wherein the amino phenol is of the formula

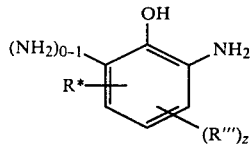

wherein R* is a substantially saturated hydrocarbon-based group having an average of from about 30 to about 750 aliphatic carbon atoms and R''' is a lower alkyl, lower alkoxyl, nitro group or halogen atom and z is 0 or 1 with the proviso that when there is only one —$NH_2$ group ortho to the phenolic OH group, R''', if present, can be ortho to said —OH group.

9. A composition according to claims 1, 3, 5, 7 or 8 wherein the ester is derived from a polyol and a high molecular weight succinic acid acylating agent containing at least 50 carbon atoms in the acyl moiety.

10. A composition according to claim 9 wherein the high molecular weight succinic acid acylating agent is an alkenyl- or alkyl succinic acid or anhydride or mixtures thereof wherein the alkenyl or alkyl group contains from 50 to 700 carbon atoms and the polyol contains at least 3 hydroxy groups.

11. A composition according to claim 9 wherein the high molecular weight succinic acid acylating agent is polyisobutenyl substituted succinic anhydride and the polyols are glycerol, pentaerythritol, mannitol or mixtures of two or more of these polyols.

12. A composition according to claim 1 wherein, when said ester composition contains unesterified acidic groups in the acylating agent, said ester composition is further reacted with an amine compound.

13. A fuel composition containing a major proportion of a normally liquid fuel and about 1 to about 10,000 parts by weight per million parts of fuel of at least one composition claimed in claim 1.

14. A fuel composition containing a major proportion of a normally liquid fuel and about 1 to about 10,000 parts by weight per million parts of fuel of at least one composition claimed in 9.

15. A fuel composition containing a major proportion of a normally liquid fuel and about 1 to about 10,000 parts by weight per million parts of fuel of at least one composition claimed in claim 12.

16. A lubricant composition comprising a major proportion of at least one oil of lubricating viscosity and about 0.05 to about 30 parts by weight per 100 parts oil of at least one composition claimed in claim 1.

17. A lubricant composition comprising a major proportion of at least one oil of lubricating viscosity and about 0.05 to about 30 parts by weight per 100 parts oil of at least one composition claimed in claim 9.

18. A lubricant composition comprising a major proportion of at least one oil of lubricating viscosity and about 0.05 to about 30 parts by weight per 100 parts oil of at least one composition claimed in claim 12.

19. An additive concentrate comprising about 30–90% of at least one composition of claim 1 and a substantially inert, normally liquid organic solvent/diluent.

20. An additive concentrate comprising about 30–90% of at least one composition of claim 9 and a substantially inert, normally liquid organic solvent/diluent.

21. An additive concentrate comprising about 30–90% of at least one composition of claim 12 and a substantially inert, normally liquid organic solvent/diluent.

* * * * *